United States Patent
Tsukada et al.

(10) Patent No.: US 11,795,427 B2
(45) Date of Patent: Oct. 24, 2023

(54) CULTURE VESSEL AND CELL CULTURE DEVICE

(71) Applicants: Sumitomo Bakelite Co., Ltd., Tokyo (JP); Hitachi, Ltd., Tokyo (JP)

(72) Inventors: Ryohei Tsukada, Tokyo (JP); Toru Yakabe, Tokyo (JP); Haruo Okubo, Tokyo (JP); Masaharu Kiyama, Tokyo (JP); Midori Kato, Tokyo (JP); Hikaru Saito, Tokyo (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 526 days.

(21) Appl. No.: 16/982,802

(22) PCT Filed: Mar. 22, 2019

(86) PCT No.: PCT/JP2019/012013
§ 371 (c)(1),
(2) Date: Sep. 21, 2020

(87) PCT Pub. No.: WO2019/182094
PCT Pub. Date: Sep. 26, 2019

(65) Prior Publication Data
US 2021/0002600 A1 Jan. 7, 2021

(30) Foreign Application Priority Data
Mar. 23, 2018 (JP) .................................. 2018-056804

(51) Int. Cl.
*C12M 1/00* (2006.01)
*C12M 1/12* (2006.01)

(52) U.S. Cl.
CPC ............ *C12M 29/06* (2013.01); *C12M 23/06* (2013.01); *C12M 23/38* (2013.01); *C12M 29/20* (2013.01)

(58) Field of Classification Search
CPC ............................. C12M 29/06; C12M 23/08
See application file for complete search history.

(56) References Cited

U.S. PATENT DOCUMENTS

| | | | |
|---|---|---|---|
| 7,867,761 B2* | 1/2011 | Esser | C12M 23/48 435/303.1 |
| 9,005,550 B2* | 4/2015 | Carter | C12M 23/40 422/547 |
| 2007/0031963 A1* | 2/2007 | Chang | C12M 23/08 435/304.2 |
| 2007/0172945 A1* | 7/2007 | O'Kennedy | C12M 29/18 435/325 |

(Continued)

FOREIGN PATENT DOCUMENTS

JP 2006204263 A 8/2006

*Primary Examiner* — Jonathan M Hurst
(74) *Attorney, Agent, or Firm* — THE WEBB LAW FIRM

(57) ABSTRACT

A culture vessel that can suppress foaming in a culture medium when a common nozzle is used to supply a liquid culture medium and a gas together. This culture vessel includes: a vessel body having an opening portion that communicates with a housing space; a lid that closes the opening portion; and a nozzle that passes through the and extends to the housing space, and supplies a liquid culture medium and a gas together. The nozzle has a vent opening portion that is formed so as to open in a side of the nozzle and serves as a movement path of the gas from inside of the nozzle into the housing space.

18 Claims, 7 Drawing Sheets

(56) References Cited

U.S. PATENT DOCUMENTS

| 2008/0032396 | A1* | 2/2008 | Chokshi | C12M 33/14 |
| | | | | 435/296.1 |
| 2009/0191620 | A1* | 7/2009 | Martin | C12M 23/04 |
| | | | | 435/294.1 |
| 2014/0349392 | A1* | 11/2014 | Nelissen | C12M 25/06 |
| | | | | 435/325 |

* cited by examiner

CULTURE VESSEL AND CELL CULTURE DEVICE

CROSS-REFERENCE TO RELATED APPLICATIONS

This application is the United States national phase of International Application No. PCT/JP2019/012013 filed Mar. 22, 2019, and claims priority to Japanese Patent Application No. 2018-056804 filed Mar. 23, 2018, the disclosures of which are hereby incorporated by reference in their entirety.

TECHNICAL FIELD

The present invention relates to a culture vessel and a cell culture device for culturing cells within a housing space.

BACKGROUND ART

The culture vessel is supplied with a culture medium (liquid culture medium) that serves as a cell growth environment, and a gas (carbon dioxide) for appropriately maintaining the growth environment. An example of such a culture vessel is disclosed in Patent Document 1 (JP 2006-204263A) described below. As shown in FIG. 7 of Patent Document 1, a culture vessel 30' is provided with an opening portion 38 to which a tube 40 for supplying a culture medium B is connected. The culture medium B is supplied from the opening portion 38 to a housing space of the culture vessel 30'. Then, the gas G is supplied from an opening portion 36 provided at a different location than the opening portion 38 for supplying the culture medium B.

Here, from the viewpoint of reducing the cost of the device that is the supply source of the culture medium and the gas, and the culture vessel, it is considered to supply the culture medium and the gas together from one location (opening portion) in the culture vessel. For example, it is conceivable to supply the culture medium and the gas using a single nozzle that extends into the housing space.

In this case, when supplying the culture medium, the culture medium may foam due to impacts when dripping. In order to suppress this, it is conceivable to supply the culture medium using a nozzle that extends to the vicinity of the bottom portion of the culture vessel. However, even in this case, when a tip portion of the nozzle is immersed under the liquid surface of the culture medium, the gas is supplied below the liquid surface, so foaming of the culture medium occurs.

PRIOR ART DOCUMENTS

Patent Documents

Patent Document 1: JP 2006-204263A

DISCLOSURE OF THE INVENTION

Problems to be Solved by the Invention

There is a demand for a culture vessel that can suppress foaming in a culture medium when a common nozzle is used to supply a liquid culture medium and a gas together.

Means for Solving Problems

A culture vessel according to the present invention is a culture vessel having a housing space inside and used to culture cells within the housing space, the culture vessel including:

a vessel body having an opening portion that communicates with the housing space;

a lid that closes the opening portion; and a nozzle that passes through the lid and extends to the housing space, and supplies a liquid culture medium and a gas together, wherein the nozzle has a vent opening portion that is formed so as to open in a side wall of the nozzle and serves as a movement path of the gas from inside of the nozzle into the housing space.

According to this configuration, the gas can be supplied into the housing space from the vent opening portion, and as a result, a portion that supplies the liquid culture medium (hereinafter, simply referred to as the "culture medium") and a portion that supplies the gas can be disposed at different locations in the nozzle. Thus, it is possible to adopt a configuration such that the portion that supplies the culture medium in the nozzle extends to the vicinity of the bottom portion of the culture vessel in order to soften impacts when dripping the culture medium, and it is also possible to dispose the vent opening portion above the liquid surface of the culture medium even in a case where the portion that supplies the culture medium is immersed under the liquid surface of the culture medium. In this way, according to the present configuration, it is possible to adopt a configuration in which impacts when dripping the culture medium are softened, and in which it is possible to suppress foaming of the culture medium that is due to supply of the culture medium itself. Also, it is possible to adopt a configuration in which the gas can be supplied above the liquid surface of the culture medium, and in which it is possible to suppress foaming of the culture medium that is due to supply of the gas. Therefore, it is possible to suppress foaming of the culture medium in a case where the culture medium and the gas are supplied together using a common nozzle.

A cell culture device according to the present invention is a cell culture device that includes a liquid feeding portion that supplies a liquid culture medium to a housing space of a culture vessel that cultures cells within the housing space, a liquid discharging portion that discharges the liquid culture medium from the housing space, a gas feeding portion that supplies gas to the housing space, a gas discharging portion that discharges the gas from the housing space, and a heat retaining portion that retains heat of the culture vessel, the cell culture device being configured such that the liquid culture medium supplied from the liquid feeding portion and the gas supplied from the gas feeding portion are merged and supplied together, wherein the culture vessel includes a vessel body having an opening portion that communicates with the housing space, a lid that closes the opening portion, and a nozzle for supply that passes through the lid and extends to the housing space, and the nozzle has a vent opening portion that is formed so as to open in a side wall of the nozzle and serves as a movement path of the gas from inside of the nozzle into the housing space.

According to this configuration, it is possible to culture the cells automatically in the culture vessel with the culture vessel set in the cell culture device by supplying/discharging the culture medium and the gas into/from the culture vessel as needed while maintaining heat of the culture vessel. At this time, by supplying together the culture medium supplied from the liquid feeding portion and the gas supplied from the gas feeding portion, it is possible to achieve simplification of the device configuration.

Also, even when the culture medium and the gas are supplied together from the cell culture device side, in the culture vessel, the gas can be supplied to the housing space from the vent opening portion, and as a result, a portion that supplies the culture medium and a portion that supplies the gas can be disposed at different locations in the nozzle. Thus, it is possible to adopt a configuration such that the portion that supplies the culture medium in the nozzle extends to the vicinity of the bottom portion of the culture vessel in order to soften impacts when dripping the culture medium, and it is also possible to dispose the vent opening portion above the liquid surface of the culture medium even in a case where the portion that supplies the culture medium is immersed under the liquid surface of the culture medium. In this way, according to the present configuration, in the culture vessel, it is possible to adopt a configuration in which impacts when dripping the culture medium are softened, and in which it is possible to suppress foaming of the culture medium that is due to supply of the culture medium itself. Also, it is possible to adopt a configuration in which the gas can be supplied above the liquid surface of the culture medium, and in which it is possible to suppress foaming of the culture medium that is due to supply of the gas. Therefore, while achieving simplification of the cell culture device, it is possible to suppress foaming of the culture medium within the culture vessel.

Following is a description of exemplary embodiments of the present invention. However, the scope of the present invention is not limited by the exemplary embodiments described below.

In one aspect of the invention, the vessel body has a ceiling portion that covers above the housing space, and the vent opening portion is formed so as to include an area above the ceiling portion.

In one aspect of the invention, the vent opening portion is configured with a side wall opening portion formed continuously or discontinuously from a tip opening portion provided in a tip portion of the nozzle.

In one aspect of the invention, the nozzle, on an inner face of the side wall, has a rib portion that protrudes toward an axial center of the nozzle, and the rib portion is formed across a boundary portion between a formation area where the vent opening portion is formed in the axial direction of the nozzle and a non-formation area where the vent opening portion is not formed.

In one aspect of the invention, the lid includes an inner lid formed integrally with the nozzle, and an outer lid that is provided separately from the inner lid and fixes the inner lid by pressing the inner lid against the vessel body.

In one aspect of the invention, the vessel body has a ceiling portion that covers above the housing space and a peripheral wall portion that covers the periphery of the housing space.

In one aspect of the invention, the vessel body has a tubular portion that protrudes from the ceiling portion or the peripheral wall portion, and that protruding end forms the opening portion.

In one aspect of the invention, the nozzle is provided so as to pass through a central position of the lid.

In one aspect of the invention, the vessel body has a bottom portion that covers below the housing space, and a cell culture area is provided in a central side of the bottom portion, and a culture medium guide portion inclined downward toward the cell culture area is formed at a peripheral edge of the cell culture area.

In one aspect of the invention, the vessel body has a ceiling portion that covers above the housing space, and a tubular portion that protrudes from the ceiling portion, that protruding end forming the opening portion, the tubular portion being formed so as to protrude upward from the ceiling portion, and the tubular portion and the nozzle being disposed at a position overlapping the culture medium guide portion when viewed in the vertical direction.

Further features and advantages of the present invention will become more apparent by the following description of exemplary and non-limiting embodiments described with reference to drawings.

BEST MODE FOR CARRYING OUT THE INVENTION

First Embodiment

Figure 1:
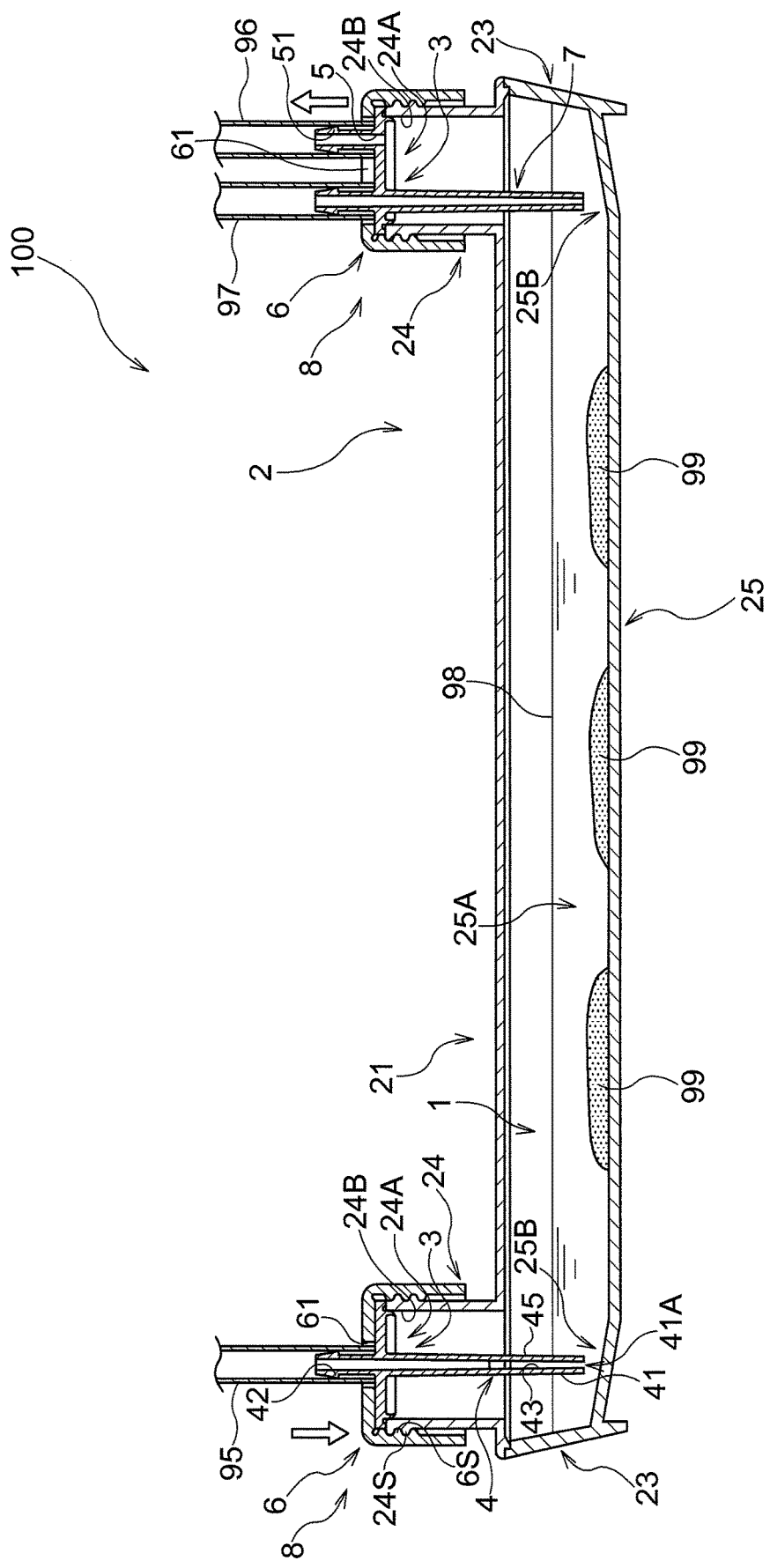
FIG. 1 is a cross-sectional view of a culture vessel.

A first embodiment of a culture vessel will be described with reference to the drawings. As shown in FIG. 1, a culture vessel 100 has a housing space 1 inside and is used to culture cells 99 within the housing space 1. The housing space 1 houses the cells 99 and a culture medium 98 for supplying nutrients to the cells 99. The components of the culture medium 98 can be appropriately changed depending on the purpose of the culture. Further, a liquid culture medium (including a semi-liquid culture medium or the like) can be used as the culture medium 98. In the present embodiment, a liquid culture medium having high fluidity is used as the culture medium 98.

The culture vessel 100 includes a vessel body 2 having an opening portion 24A that communicates with the housing space 1, and a lid 8 that closes the opening portion 24A. By closing the opening portion 24A with the lid 8, airtightness of the housing space 1 can be secured. In the present embodiment, the lid 8 includes an inner lid 3 that closes the opening portion 24A, and an outer lid 6 that is provided separately from the inner lid 3 and presses the inner lid 3 against the vessel body 2.

Figure 2:
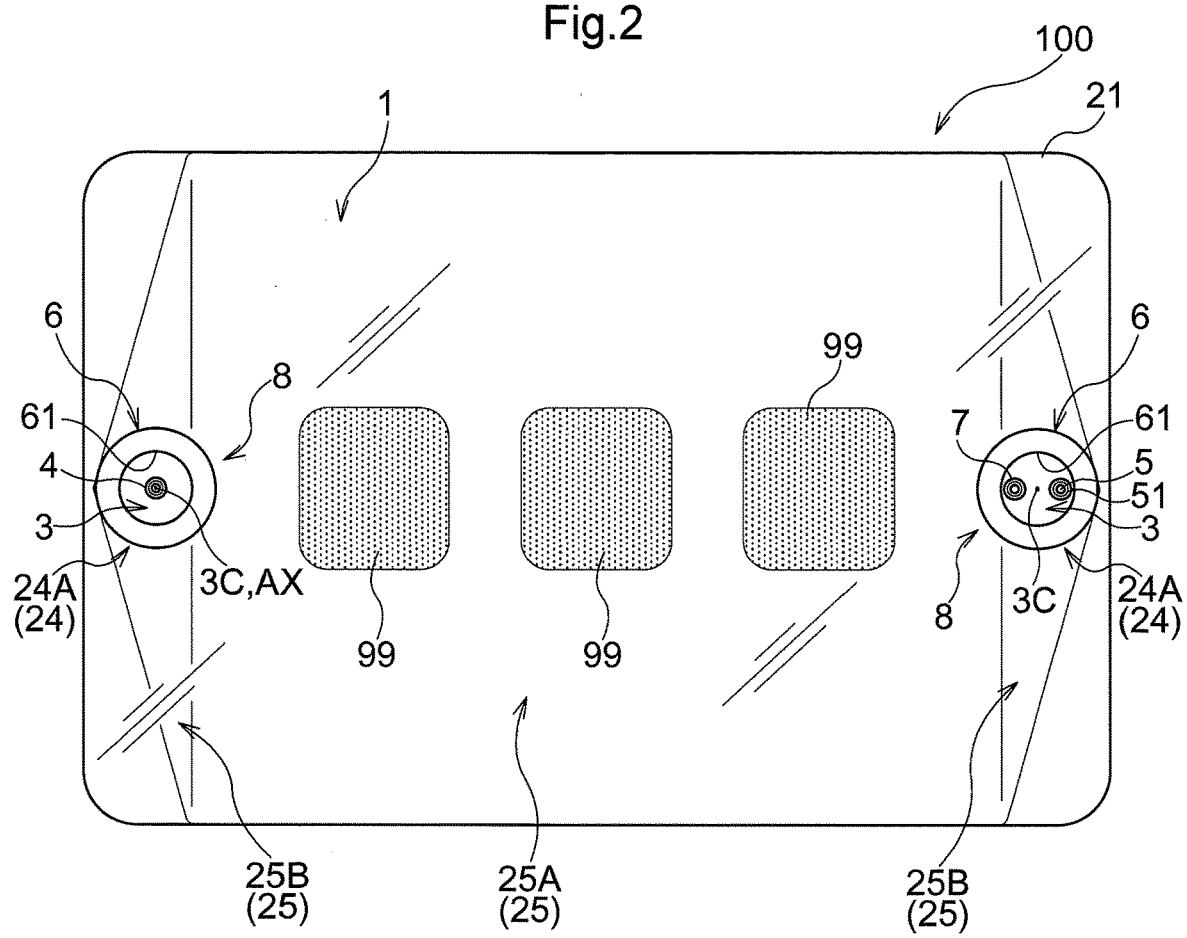
FIG. 2 is a vertical view (plan view) of the culture vessel.

As shown in FIGS. 1 and 2, the vessel body 2 includes a ceiling portion 21 that covers above the housing space 1, a plurality of peripheral wall portions 23 that cover the periphery of the housing space 1, and a bottom portion 25 that covers below the housing space 1. In the present embodiment, the vessel body 2 is formed in a rectangular shape when viewed in the vertical direction, and has four of the peripheral wall portions 23. Also, the housing space 1 is formed surrounded by the ceiling portion 21, the bottom portion 25, and the four peripheral wall portions 23. Note that, for example, polyethylene, polypropylene, or the like can be adopted as the material of the vessel body 2.

The peripheral wall portions 23 are configured to incline inward toward the bottom. Therefore, the four peripheral wall portions 23 are generally configured to constrict inward toward the bottom. As a result, the area lower in the housing space 1 can be made narrower, so even with a small amount of the culture medium 98, the area lower in the housing space 1 can be easily filled with the culture medium 98. Therefore, the culture medium 98 can be easily spread over the cells 99 disposed in the area lower in the housing space 1.

The bottom portion 25 is provided with a cell culture area 25A where the cells 99 are disposed and culture medium guide portions 25B that guide the culture medium 98 to the cell culture area 25A. In the illustrated example, the cell culture area 25A is provided in a central side of the bottom portion 25. The culture medium guide portions 25B are formed at peripheral edges of the cell culture area 25A so as to be inclined downward toward the cell culture area 25A. Thus, the culture medium 98 can be appropriately guided to the cell culture area 25A disposed in the central side of the bottom portion 25. In the example shown in FIG. 2, the culture medium guide portions 25B are formed so as to gradually expand toward the cell culture area 25A when viewed in the vertical direction. Specifically, the culture medium guiding portions 25B are formed in a triangular shape (more specifically, an isosceles triangular shape) having a cell culture area 25A side as a bottom side when viewed in the vertical direction. Thus it is easier to spread the culture medium 98 over the entire cell culture area 25A.

In the present embodiment, a surface treatment (for example, hydrophilization treatment) is applied to the portion of the bottom portion 25 corresponding to the cell culture area 25A. This makes it easier to adhere the cells 99 to the cell culture area 25A. Such a configuration is suitable when performing so-called adhesion culturing. In the illustrated example, the cells 99 are disposed in the cell culture area 25A by adhering to the cell culture area 25A. However, the culture vessel 100 can also be used when performing so-called suspension culturing. In this case, the cell culture area 25A is an area having a predetermined height, and the cells 99 are disposed in the cell culture area 25A in a state of being suspended in the cell culture area 25A.

The vessel body 2 has a tubular portion 24 that protrudes from the ceiling portion 21 or a peripheral wall portion 23, and has a protruding end that forms the opening portion 24A. In the present embodiment, the tubular portion 24 is formed so as to protrude upward from the ceiling portion 21. In the illustrated example, the upper end of the tubular portion 24 forms the opening portion 24A, and the lower end of the tubular portion 24 is connected to the ceiling portion 21. Further, in this example, the tubular portion 24 is formed in a cylindrical shape, and has a male screw portion 24S on the outer peripheral surface of the tubular portion 24. Since the opening portion 24A is formed at the protruding end of the tubular portion 24, the inner lid 3 that closes the opening portion 24A can be easily attached.

As shown in FIG. 1, in the present embodiment, the vessel body 2 has a pair of the openings 24A. One of the pair of opening portions 24A is for supplying the culture medium 98 and a gas into the housing space 1, and the other is for discharging the culture medium 98 and the gas in the housing space 1 from the housing space 1. By supplying and discharging the culture medium 98 and the gas through the pair of opening portions 24A, the culture vessel 100 can maintain the growth environment of the cells 99 in the housing space 1 under predetermined conditions. Therefore, the culture vessel 100 according to the present embodiment is suitable for supplying and discharging the culture medium 98 while various components are fixed, without removing those components. In the following description, of the pair of opening portions 24A, the opening portion 24A for supplying the culture medium 98 and the gas into the housing space 1 (the opening portion 24A on the left side in FIG. 1) will be referred to as the "supply opening portion 24A". The opening portion 24A for discharging the culture medium 98 and the gas in the housing space 1 from the housing space 1 (the opening portion 24A on the right side in FIG. 1) will be referred to as the "discharge opening portion 24A".

First, the configuration in the vicinity of the discharge opening portion 24A will be described with reference to FIGS. 1 to 3.

The inner lid 3 closes the opening portion 24A formed in the vessel body 2. As shown in FIG. 3, in the present embodiment, the inner lid 3 has a fitting portion 31 that protrudes toward the inside of the vessel body 2 in a state with the opening portion 24A closed. The fitting portion 31 is configured to contact an entire tubular inner peripheral face 24B formed on the inner face of the tubular portion 24 in the circumferential direction in a state where the inner lid 3 closes the opening portion 24A. A taper portion 31A is formed in a tip portion of the fitting portion 31 so as to narrow toward an inner lid center 3C side toward the tip side. The taper portion 31A has a function of guiding the fitting portion 31 to the opening portion 24A when closing the opening portion 24A with the inner lid 3. Note that, in the present embodiment, the inner lid center 3C indicates the center of the inner lid 3 when viewed in the vertical direction (see FIG. 2).

The inner lid 3 has a vessel-side contact portion 32 that contacts the tubular portion 24 (vessel body 2) from above. The vessel-side contact portion 32 is formed in the bottom face portion of the inner lid 3 so as to surround the outer periphery of the fitting portion 31. The inner lid 3 also has an outer lid-side contact portion 33 that contacts an outer lid 6 described later from below. The outer lid-side contact portion 33 is formed at the peripheral edge of the upper face portion of the inner lid 3.

The culture vessel 100 is provided with a discharge nozzle 7 for discharging gas, which passes through the lid 8 and extends to the housing space 1. In the present embodiment, the discharge nozzle 7 passes through the inner lid 3 that closes the discharge opening portion 24A and extends to the housing space 1. The inner lid 3 that closes the discharge opening portion 24A is formed integrally with the discharge nozzle 7.

The discharge nozzle 7 protrudes inward and outward of the vessel body 2 in a state with the inner lid 3 closing the discharge opening portion 24A. A portion of the discharge nozzle 7 that protrudes inward of the vessel body 2 is disposed in the housing space 1. A liquid feeding pipe 97 is connected to a portion of the discharge nozzle 7 that protrudes outward from the vessel body 2. The liquid feeding pipe 97 is a pipe through which the culture medium 98 flows. In the present embodiment, the culture medium 98 discharged from the housing space 1 flows through the liquid feeding pipe 97.

As shown in FIG. 2, in the present embodiment, the discharge nozzle 7 is provided at a position eccentric to the inner lid center 3C of the inner lid 3. The discharge nozzle 7 is eccentric to the central side of the vessel body 2 with respect to the inner lid center 3C. Here, FIG. 1 shows an example in which the discharge nozzle 7 and a supply nozzle 4 described later are configured to have the same length. However, as described above, since the discharge nozzle 7 is eccentric to the central side of the vessel body 2 with respect to the inner lid center 3C, it is possible to dispose the discharge nozzle 7 extending lower, while preventing the discharge nozzle 7 from contacting the inclined face of the culture medium guide portions 25B, for example. In other words, the discharge nozzle 7 may be disposed so as to extend further downward than the supply nozzle 4. As a result, the culture medium 98 stored below the housing space 1 can be appropriately discharged.

As shown in FIG. 1, in the present embodiment, the inner lid 3 that closes the discharge opening portion 24A is provided with a vent hole 5 for discharging gas in a state with the vent hole 5 passing through the inner lid 3. Thus, the gas can be discharged from the housing space 1. In the illustrated example, the vent hole 5 is provided at a position eccentric to the inner lid center 3C of the inner lid 3. In this way, by making the discharge nozzle 7 and the vent hole 5 eccentric with respect to the inner lid center 3C, it becomes easy to dispose flow paths of the culture medium 98 and the gas separately in the inner lid 3. Further, for example, it becomes easy to provide a plurality of the discharge nozzles 7 and a plurality of the vent holes 5 described later for one inner lid 3.

In the present embodiment, the vent hole 5 has a pipe connecting portion 51 for connecting a gas feeding pipe 96. The pipe connecting portion 51 protrudes toward the outside of the vessel body 2 in a state with the inner lid 3 closing the discharge opening portion 24A. This facilitates the connection of the gas feeding pipe 96 to the pipe connecting portion 51. The gas discharged from the housing space 1 flows through the gas feeding pipe 96. However, the above-described configuration is not a limitation, and a configuration may also be adopted in which the vent hole 5 does not have the pipe connecting portion 51. In this case, the vent hole 5 and the gas feeding pipe 96 are directly connected.

As described above, the culture vessel 100 includes the outer lid 6 that is provided separately from the inner lid 3 and fixes the inner lid 3 by pressing the inner lid 3 against the vessel body 2. Thus, airtightness of the housing space 1 can be improved. In the present embodiment, the outer lid 6 has a central opening portion 61 that passes through the central side of the outer lid 6 in the vertical direction. The discharge nozzle 7 and the pipe connecting portion 51 protrude to the outside of the vessel body 2 through the central opening portion 61. The central opening portion 61 is formed to be smaller than the inner lid 3 when viewed in the vertical direction. As a result, the outer lid 6, while allowing the discharge nozzle 7 and the pipe connecting portion 51 to protrude to the outside of the vessel body 2 with the central opening portion 61, can fix the inner lid 3 by pressing against the inner lid 3 from above with other portions.

Figure 3:
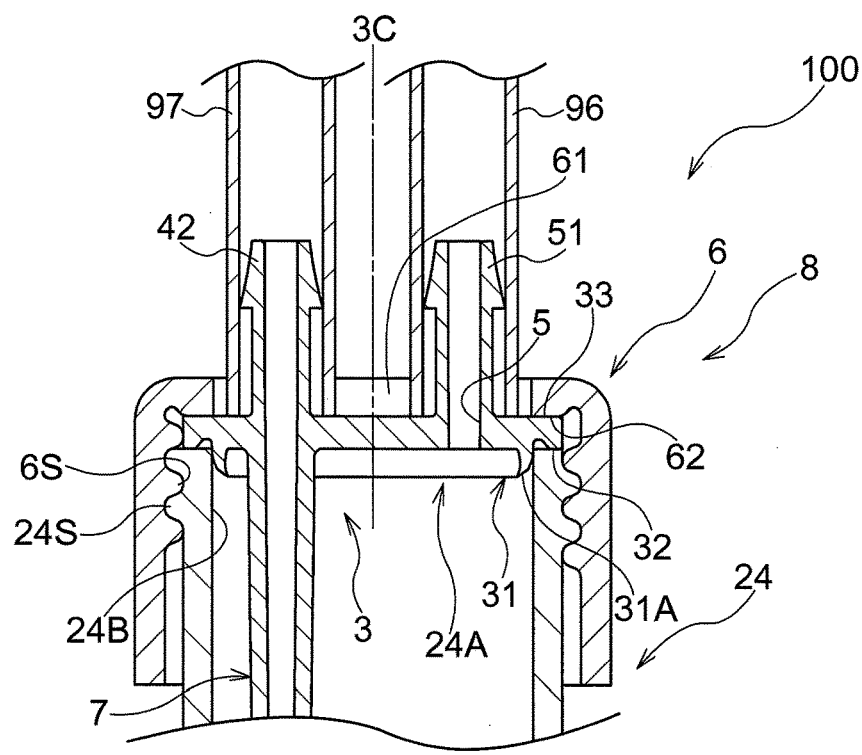
FIG. 3 is an enlarged cross-sectional view of main parts showing the vicinity of an opening portion for discharge.
Figure 4:
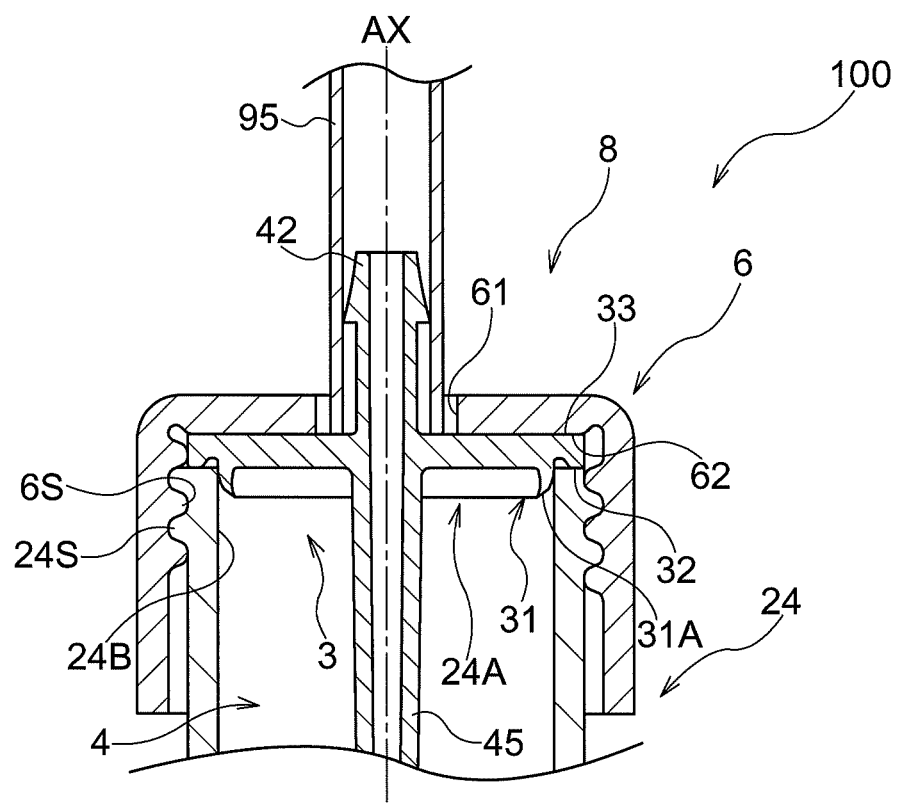
FIG. 4 is an enlarged cross-sectional view of main parts showing the vicinity of an opening portion for supply.

As shown in FIG. 3, in the present embodiment, the outer lid 6 has a pressing portion 62 that presses and fixes the inner lid 3. The pressing portion 62 is configured to face downward in a state where the tubular portion 24 is covered with the outer lid 6, and contacts the inner lid 3 from above. In the example shown in FIG. 3, the pressing portion 62 is configured to contact the outer lid-side contact portion 33 of the inner lid 3.

In the present embodiment, the outer lid 6 is configured to press and fix the inner lid 3 by rotational operation of the outer lid 6 in a state where the tubular portion 24 is covered with the outer lid 6. As shown in FIG. 3, the outer lid 6 has a female screw portion 6S that meshes with the male screw portion 24S of the tubular portion 24, and thereby can be screwed to the tubular portion 24. In a state where the pressing portion 62 of the outer lid 6 and the outer lid-side contact portion 33 of the inner lid 3 are in contact with each other, by rotationally operating the outer lid 6 in the screwing direction, it is possible to more strongly put the pressing portion 62 in contact with the outer lid-side contact portion 33, and thus the inner lid 3 can be more firmly fixed to the opening portion 24A (tubular portion 24). This makes it possible to further improve the airtightness of the housing space 1.

As described above, in the culture vessel 100, the inner lid 3 and the outer lid 6 capable of appropriately sealing the housing space 1 are separate bodies. Therefore, the inner lid 3 and the outer lid 6 can be separately molded, and therefore it is easy to realize a culture vessel 100 that is easy to manufacture as a whole.

Further, since the discharge nozzle 7 is provided at a position eccentric with respect to the inner lid center 3C in the inner lid 3, it is easy to dispose flow paths of the culture medium 98 and the gas separately in the inner lid 3.

For example, when the discharge nozzle 7 is eccentrically disposed with respect to the inner lid center 3C, and the inner lid 3 and the outer lid 6 are integrated, the discharge nozzle 7 also rotates around the inner lid center 3C by rotational operation when screwing. In this case, the rotating discharge nozzle 7 is more likely to come into contact with the inclined face of the culture medium guide portions 25B, and if this happens, the discharge nozzle 7 may be damaged or the bottom portion 25 (culture medium guide portions 25B) of the vessel body 2 may be scraped. However, in the present embodiment, as described above, the inner lid 3 where the discharge nozzle 7 is formed and the outer lid 6 are separate bodies, so the inner lid 3 is not rotated even by the rotational operation of the outer lid 6, and it is possible to firmly fix the inner lid 3 to the opening portion 24A (tubular portion 24). As a result, while enabling appropriate discharge of the culture medium 98 and reliable sealing of the housing space 1, it is possible to suppress contact of the discharge nozzle 7 with the bottom portion 25 (culture medium guide portions 25B) of the vessel body 2 when screwing the outer lid 6.

Next, the configuration in the vicinity of the supply opening portion 24A will be described with reference to FIGS. 1, 2 and 4 to 6. Note that the configurations of the lid 8, the tubular portion 24, and the like are substantially the same as the configurations in the vicinity of the discharge opening portion 24A described above, and therefore mainly the different points will be described below.

The culture vessel 100 is provided with the supply nozzle 4 for supplying the culture medium 98 and the gas, which passes through the lid 8 and extends to the housing space 1. The supply nozzle 4 is a common nozzle for supplying the culture medium 98 and the gas together. In the present embodiment, the supply nozzle 4 corresponds to a "nozzle". In the present embodiment, the supply nozzle 4 passes through the inner lid 3 that closes the supply opening portion 24A and extends to the housing space 1. The inner lid 3 that closes the supply opening 24A is formed integrally with the supply nozzle 4.

In the present embodiment, the supply nozzle 4 is provided so as to pass through the central position of the lid 8. In the example shown in FIG. 2, the supply nozzle 4 is provided so as to pass through the inner lid center 3C of the inner lid 3. The supply nozzle 4 is formed in a tubular shape, and is disposed such that an axial center AX of the supply nozzle 4 and the inner lid center 3C overlap each other when viewed in the vertical direction.

The supply nozzle 4 protrudes inward and outward of the vessel body 2 in a state with the inner lid 3 closing the opening portion 24A. In the present embodiment, the supply nozzle 4 has an inside tip portion 41 (first tip portion), which is a tip portion on the inner side of the vessel body 2 in the supply nozzle 4, and an outside tip portion 42 (second tip portion), which is a tip portion on the outer side of the vessel body 2 in the supply nozzle 4. The inside tip portion 41 is disposed inside the housing space 1, and the outside tip portion 42 is disposed outside the housing space 1. A liquid/gas feeding pipe 95 is connected to the outside tip portion 42. The liquid/gas feeding pipe 95 is a pipe through which the culture medium 98 and the gas flow. In the present embodiment, both the culture medium 98 supplied from an unshown culture medium supply portion to the housing space 1 and the gas supplied from an unshown gas supply portion to the housing space 1 simultaneously flow in the liquid/gas feeding pipe 95.

The supply nozzle 4 has a tip opening portion 41A that opens at its tip and communicates with the housing space 1. In the present embodiment, the tip opening portion 41A is formed in the inside tip portion 41 of the supply nozzle 4. The culture medium 98 that flows through the inside of the supply nozzle 4 is supplied into the housing space 1 through the tip opening portion 41A. The tip opening portion 41A is a "liquid passage opening portion" that mainly serves as a movement path of the liquid culture medium.

As shown in FIG. 2, in the present embodiment, the tubular portion 24 and the supply nozzle 4 are disposed at a position overlapping the culture medium guide portions 25B when viewed in the vertical direction. Thus, the culture medium 98 can be appropriately supplied to the culture medium guide portions 25B, and the inclined face of the culture medium guide portions 25B can be used to appropriately guide the culture medium 98 to the cell culture area 25A. Further, the culture medium 98 supplied from the supply nozzle 4 can be prevented from directly contacting the cells 99 disposed in the cell culture area 25A, and thus damage to the cells 99 or the like can be suppressed.

Figure 5:
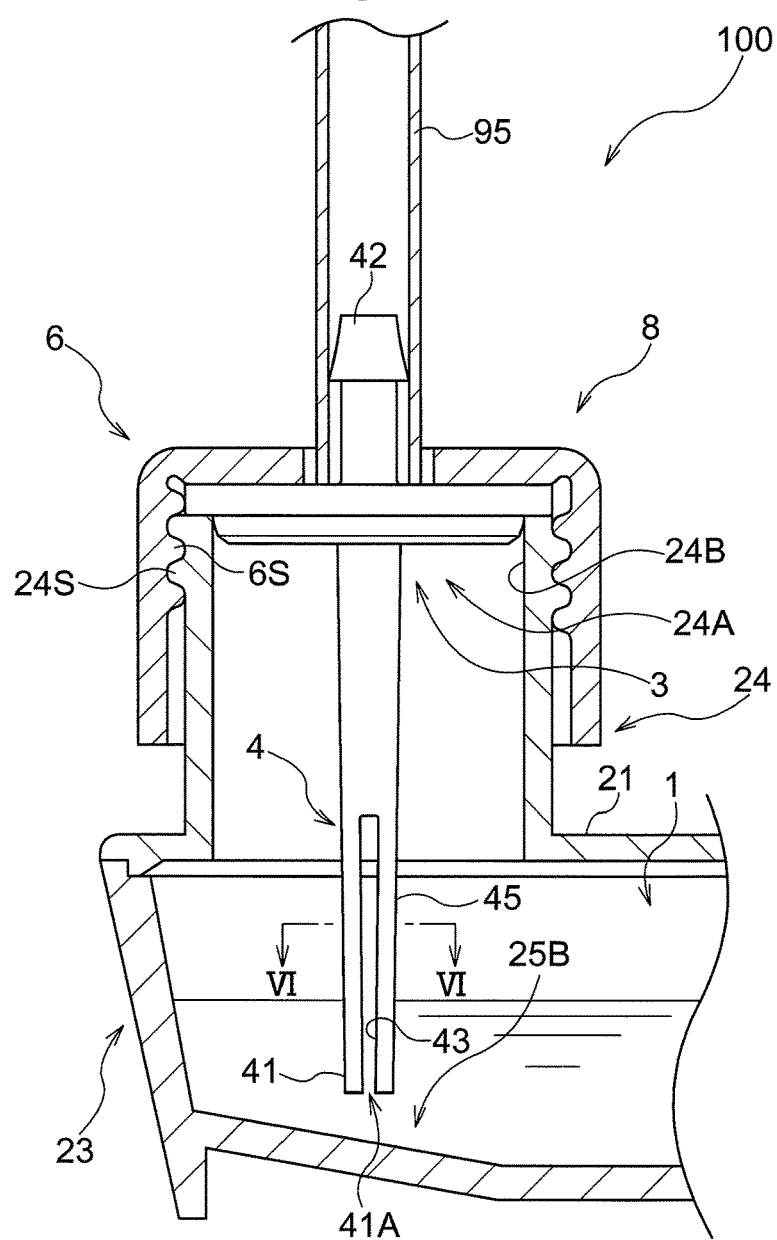
FIG. 5 is an enlarged cross-sectional view of main parts showing the vicinity of the opening portion for supply.
Figure 6:
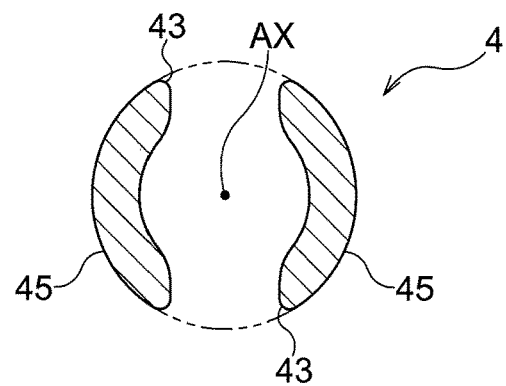
FIG. 6 is a cross-sectional view taken along line VI-VI in FIG. 5.

As shown in FIGS. 5 and 6, the supply nozzle 4 has a vent opening portion (side wall opening portion) 43 formed so as to open in the side wall 45 of the supply nozzle 4. The vent opening portion 43 is a "sideways opening portion" formed in the side wall 45 of the supply nozzle 4 so as to face sideways. The vent opening portion 43 serves as a movement path of the gas from the inside of the supply nozzle 4 into the housing space 1. As a result, a portion that supplies the culture medium 98 and a portion that supplies the gas can be disposed at different locations in the supply nozzle 4. In the present embodiment, the culture medium 98 is supplied from the tip opening portion 41A (liquid passage opening portion) of the supply nozzle 4, and the gas is supplied from the sideways opening portion (vent opening portion 43) of the supply nozzle 4.

As shown in FIG. 5, in the present embodiment, the vent opening portion 43 is formed so as to include an area above the ceiling portion 21. In other words, the upper end of the vent opening portion 43 is disposed above the ceiling portion 21. Thus, for example, even when the housing space 1 is filled with the culture medium 98 up to the vicinity of the ceiling portion 21, the gas can be supplied above the liquid surface of the culture medium 98.

In the present embodiment, the vent opening portion 43 is configured with a slit formed continuously from the tip opening portion 41A provided in the inside tip portion 41 of the supply nozzle 4. The vent opening portion 43 formed of a slit is formed along the axial center AX of the supply nozzle 4. According to this configuration, when the culture vessel 100 is manufactured, the vent opening portion 43 can be easily formed in the side wall 45 of the supply nozzle 4, so manufacturing can be facilitated. The vent opening portion 43 is suitably formed over a range of ⅓ to ⅔ of the axial direction length of the supply nozzle 4. According to this configuration, the durability of the supply nozzle 4 can be easily secured while preventing the entire vent opening portion 43 from being immersed under the liquid surface of the culture medium 98.

As shown in FIG. 6, in the present embodiment, the vent opening portion 43 is formed so as to open on both sides sandwiching the axial center AX of the supply nozzle 4. Thus, a large movement path of gas into the housing space 1 can be secured, and the gas that flows through the inside of the supply nozzle 4 can be supplied into the housing space 1 before reaching the tip opening portion 41A. However, this sort of configuration is not a limitation, and a configuration may also be adopted in which the vent opening portion 43 is formed at one location in the circumferential direction when the supply nozzle 4 is viewed from the axial direction.

As described above, the supply nozzle 4 has the vent opening portion 43 which is formed to open in the side wall 45 of the supply nozzle 4 and serves as a movement path of the gas from the inside of the supply nozzle 4 into the housing space 1. Therefore, the portion that supplies the culture medium 98 and the portion that supplies the gas can be disposed at different locations in the supply nozzle 4.

Furthermore, while the inside tip portion 41 for supplying the culture medium 98 is formed in the tip of the supply nozzle 4, the vent opening portion 43 for supplying the gas is formed so as to include the area above the ceiling portion 21. Therefore, it is possible to soften impacts when dripping the culture medium 98, and the gas can be supplied above the liquid surface of the culture medium 98. Accordingly, it is possible to suppress foaming of the culture medium 98 when supplying the culture medium 98 and the gas.

Figure 7:
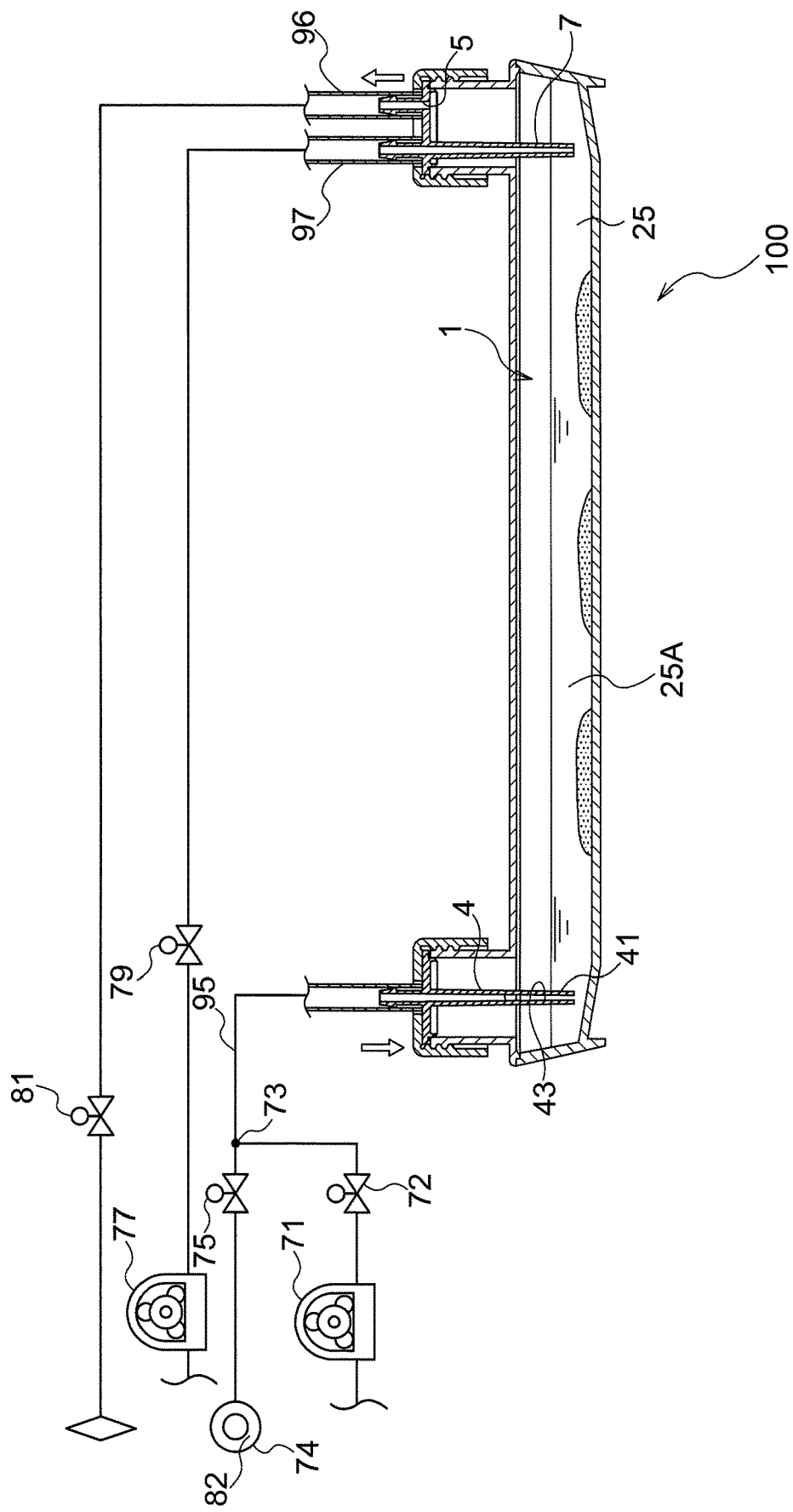
FIG. 7 is a schematic view of a cell culture device.

In the present embodiment, as described above, the supply nozzle 4 supplies the culture medium 98 and the gas together from one opening in the housing space 1. Also, discharge of the culture medium 98 and the gas from the housing space 1 is performed independently by the vent hole 5 for the gas and the discharge nozzle 7 for the liquid. FIG. 7 shows an exemplary configuration of a cell culture device that automatically performs cell culturing using this culture vessel 100. A liquid feeding portion 71 is a liquid feed pump for liquid supply to the housing space 1, with the upstream side of the liquid feeding portion 71 connected to a liquid bottle (not shown), and the downstream side of the liquid feeding portion 71 connected to a connecting portion 73 through a liquid feed control valve 72. A gas feeding portion 74 is gas feeding source for gas supply to the housing space 1, and is connected to the connecting portion 73 through a gas feed control valve 75. The connecting portion 73 is connected to the supply nozzle 4 through the liquid/gas feeding pipe 95.

A liquid discharging portion 77 is a discharge pump for liquid discharge from the housing space 1. The upstream side of the liquid discharging portion 77 connected by the liquid feeding pipe 97 is connected to the discharge nozzle 7 through a liquid discharge control valve 79, and the downstream side of the liquid discharging portion 77 is connected to a discharge bottle (not shown). The gas feeding pipe 96 is a gas discharge pipe for gas discharge connected to the vent hole 5 of the culture vessel 100. The gas feeding pipe 96 is connected to a vent filter 82 through a gas discharge control valve 81, and the downstream side of the gas feeding pipe 96 is open to the atmosphere.

In the present embodiment, when gas is fed to the housing space 1, the gas feed control valve 75 and the gas discharge control valve 81 are opened, the liquid feed control valve 72 and the liquid discharge control valve 79 continue to be in a closed state, and the gas feeding portion 74 feeds gas with a predetermined gas feed amount. Then, the fed gas passes through the gas feed control valve 75, is introduced into the housing space 1 from the supply nozzle 4 through the vent opening portion 43, passes through the gas discharge control valve 81 and the vent filter 82 from the gas feeding pipe 96, and is discharged to the atmosphere.

When feeding liquid to the housing space 1, the liquid feed control valve 72 and the gas discharge control valve 81 are opened, and a predetermined liquid feeding process is performed by the liquid feeding portion 71. As a result, the gas initially held inside the liquid/gas feeding pipe 95 passes through the vent opening portion 43 from the supply nozzle 4 and is introduced into the housing space 1, and then the desired liquid is introduced into the housing space 1 from the unshown liquid bottle. Afterward, excess gas is pushed out, and the desired liquid is fed by the liquid feeding portion 71. At this time, similarly to the above description, since the gas discharge control valve 81 is opened, an amount of gas corresponding to the sum of the introduced gas and liquid is discharged from the vent filter 82.

When discharging the liquid from the housing space 1, the gas feed control valve 75 and the liquid discharge control valve 79 are opened, and a predetermined liquid discharging process is performed by the liquid discharging portion 77, so that the gas initially held inside the liquid feeding pipe 97 passes through the liquid discharge control valve 79 and is discharged to the unshown liquid discharge bottle. After that gas, the culture medium 98 is sucked from the discharge nozzle 7, flows through the liquid feeding pipe 97, passes through the liquid discharge control valve 79, and is discharged into the liquid discharge bottle. On the other hand, at this time, the gas feed control valve 75 is opened so that gas can be fed from the gas feeding portion 74, and an amount of gas corresponding to the sum of the discharged gas and liquid is fed from the gas feeding portion 74 so it is possible to fill the inside of the housing space 1.

The cell culture device of this embodiment includes a heat retaining portion (not shown) that retains the heat of the culture vessel 100. The heat retaining portion is suitably configured with a constant temperature portion (incubator) that holds the culture vessel 100 at a constant temperature. Cell culturing is possible by holding the culture vessel 100 at a temperature suitable for cell culturing with the heat retaining portion (incubator). As described above, the cell culture device includes the liquid feeding portion 71 that feeds liquid such as the culture medium 98 to the culture vessel 100, the liquid discharging portion 77 that discharges liquid such as the culture medium 98, the gas feeding portion 74 that feeds gas for ventilation, and the gas discharging portion (gas feeding pipe 96) that discharges the gas. In this cell culture device, by placing the culture vessel 100 that suppresses foaming of the culture medium 98 when supplying the culture medium 98 and the gas together, and retaining the heat of the culture vessel 100 with the heat retaining portion (incubator), it is possible to automatically perform cell culturing.

Second Embodiment

Next, a second embodiment of the culture vessel 100 will be described with reference to FIGS. 8 and 9. Below, the culture vessel 100 according to the present embodiment will be described focusing mainly on differences from the above-described first embodiment. Note that points that are not particularly described are the same as in the above-described first embodiment.

Figure 8:
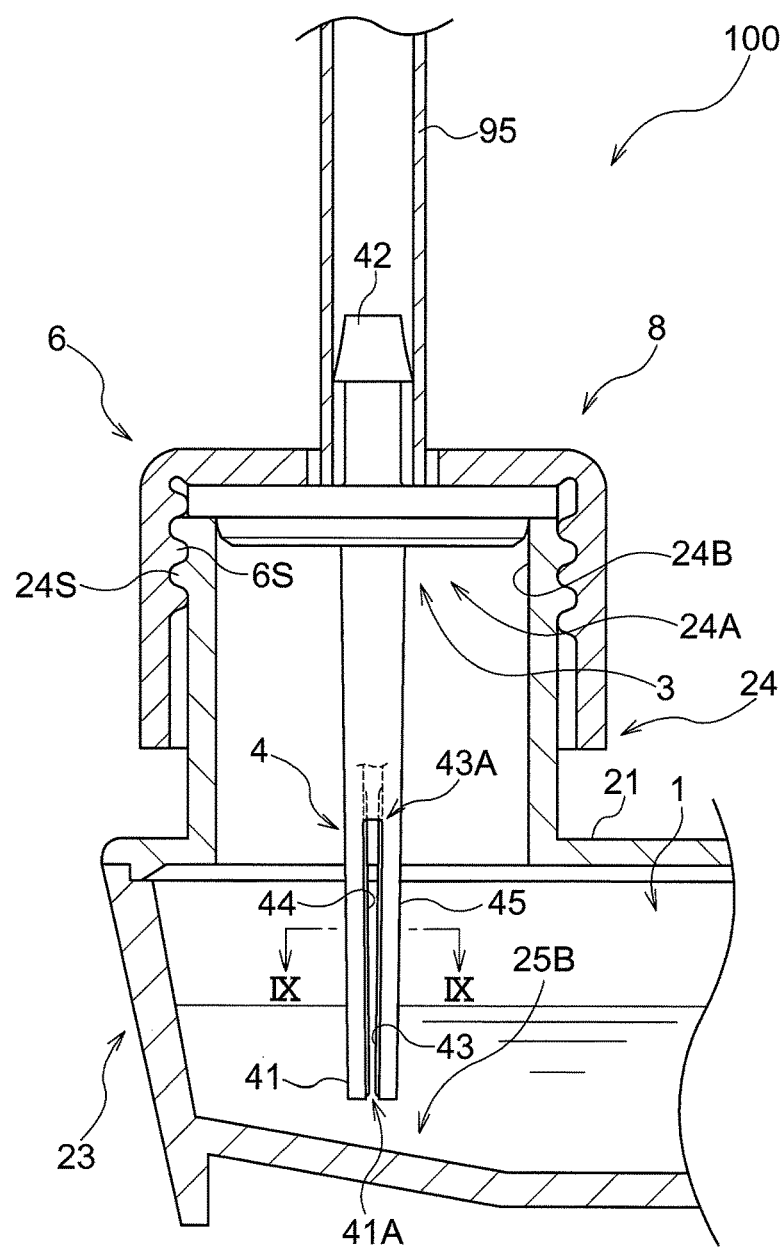
FIG. 8 is an enlarged cross-sectional view of main parts showing the vicinity of an opening portion for supply in a culture vessel according to a second embodiment.
Figure 9:
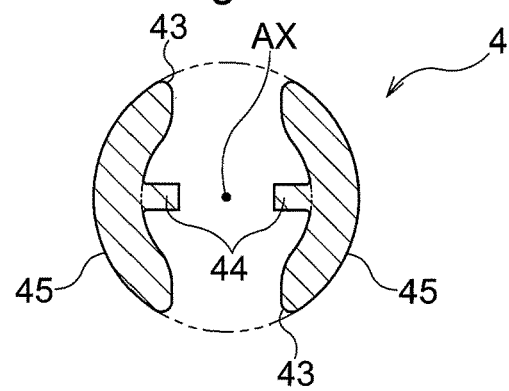
FIG. 9 is a cross-sectional view taken along line IX-IX in FIG. 8.

As shown in FIGS. 8 and 9, the supply nozzle 4 has a rib portion 44 protruding toward the axial center AX of the supply nozzle 4 on the inner face of the side wall 45 of the supply nozzle 4. The culture medium 98 flowing down the inside of the supply nozzle 4 flows through the rib portion 44 by the action of the surface tension occurring between the culture medium 98 and the rib portion 44. The rib portion 44 allows the culture medium 98 to flow through the inside of the supply nozzle 4 so as to avoid the vent opening portion 43, so the culture medium 98 can smoothly reach the tip opening portion 41A. Also, since the vent opening portion 43 is less likely to be blocked by the culture medium 98, the gas supply from the vent opening portion 43 can be smoothly performed.

As shown in FIG. 9, the rib portion 44 and the vent opening portion 43 are formed at different positions in the circumferential direction with respect to the axial center AX of the supply nozzle 4. In the illustrated example, a pair of the rib portions 44 is formed on both sides of the axial center AX at a position 90 degrees out of phase with the vent opening portion 43 which is formed to open on both sides of the axial center AX. However, this sort of configuration is not a limitation, and a configuration may also be adopted in which the rib portion 44 is formed at one location in the circumferential direction when the supply nozzle 4 is viewed from the axial direction.

As shown in FIG. 8, the rib portion 44 is formed across a boundary portion 43A between a formation area where the vent opening portion 43 is formed in the axial direction of the supply nozzle 4 and a non-formation area where the vent opening portion 43 is not formed. In other words, the rib portion 44 is formed over the upstream end of the vent opening portion 43 in the gas flow direction. With such a configuration, it is possible to appropriately guide the culture medium 98 toward the tip opening portion 41A while allowing the gas to move from the vent opening portion 43 into the housing space 1. In this embodiment, the rib portion 44 is formed from the non-formation area where the vent opening portion 43 is not formed to the tip opening portion 41A. As a result, the culture medium 98 can be guided with high certainty toward the tip opening portion 41A.

Other Embodiments (1) In the above embodiments, an example is described in which the vent opening portion 43 is configured with a slit continuously formed from the tip opening portion 41A provided in the inside tip portion 41 of the supply nozzle 4. However, such a configuration is not a limitation, and a configuration may also be adopted in which the vent opening portion 43 is formed, for example, over a range of at least $2/3$ of the axial direction length, and the vent opening portion 43 may be formed at three or more locations in the circumferential direction when the supply nozzle 4 is viewed from the axial direction. Further, the vent opening portion 43 may be formed at a location apart from the tip opening portion 41A (in other words, as an opening portion independent of the tip opening portion 41A). For example, the vent opening portion 43 may be configured with a hole portion that passes through the side wall 45 of the supply nozzle 4. In this case, the vent opening portion 43 may be configured with a plurality of hole portions. Further, the rib portion 44 is not limited to the configuration in the above-described embodiments, and for example, may be formed at three or more locations in the circumferential direction when the supply nozzle 4 is viewed from the axial direction.

Figure 10:
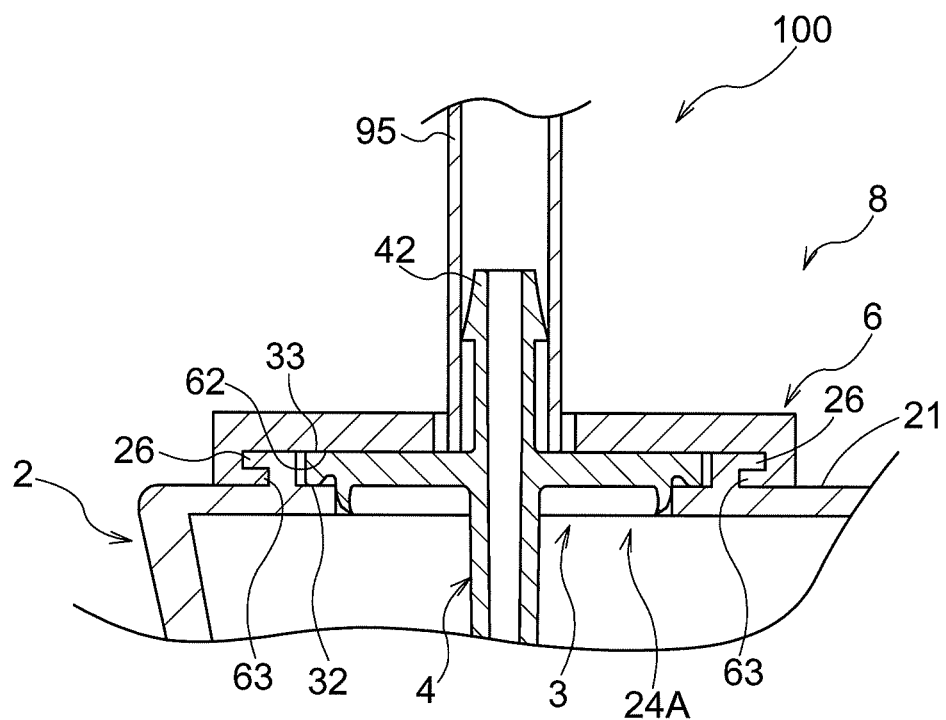
FIG. 10 is an enlarged cross-sectional view of main parts of a culture vessel according to another embodiment.

(2) In the above embodiments, an example is described in which the opening portion 24A is formed at the protruding end of the tubular portion 24 protruding from the ceiling portion 21 of the vessel body 2. However, such a configuration is not a limitation, and a configuration may also be adopted in which, as shown in FIG. 10, the opening portion 24A is directly formed in the ceiling portion 21 of the vessel body 2, and the vessel body 2 does not have a tubular portion. In this case, a locking claw 26 that locks the outer lid 6 may be formed in the vicinity of the opening portion 24A, and the outer lid 6 may be provided with a locking portion 63 that is locked to the locking claw 26. The outer lid 6 locked by the locking claw 26 abuts against the inner lid 3 from above to press and fix the inner lid 3.

(3) In the above embodiments, an example is described in which both the discharge nozzle 7 and the vent hole 5 are disposed eccentrically with respect to the inner lid center 3C. However, such a configuration is not a limitation, and a configuration may also be adopted in which either the discharge nozzle 7 or the vent hole 5 is disposed so as to be at the position of the inner lid center 3C.

(4) In the above embodiments, an example is described in which the lid 8 that closes the supply opening portion 24A includes the inner lid 3 that integrally has the supply nozzle 4 and the outer lid 6 that is separate from the inner lid 3. However, such a configuration is not a limitation, and a configuration may also be adopted in which the lid 8 is configured as an integrated body including the supply nozzle 4. A similar concept can be applied to the lid 8 that closes the discharge opening portion 24A.

(5) In the above embodiments, an example is described in which the vessel body 2 has a rectangular shape when viewed in the vertical direction. However, such a configuration is not a limitation, and a configuration may also be adopted in which the shape of the vessel body 2 when viewed in the vertical direction is polygonal or circular.

(6) The configurations disclosed in each of the above-described embodiments (including the above-described embodiments and the other embodiments; the same applies hereinafter) can be applied in combination with the configurations disclosed in other embodiments unless there is some contradiction. Regarding such other configurations, the embodiments disclosed in the present specification are in all respects disclosed as examples, and can be appropriately modified without departing from the gist of the present disclosure.

DESCRIPTION OF REFERENCE SIGNS

100: culture vessel
1: housing space
2: vessel body
3: inner lid
3C: inner lid center
4: supply nozzle (nozzle)
6: outer lid
8: lid
21: ceiling portion
23: peripheral wall portion
24: tubular portion
24A: opening portion
25: bottom portion
25A: cell culture area
25B: culture medium guide portion
41: inside tip portion (nozzle tip portion)
41A: tip opening portion
43: vent opening portion
44: rib portion
45: side wall
98: culture medium
99: cell
AX: axial center

The invention claimed is:

1. A culture vessel having a housing space inside and used to culture cells within the housing space, the culture vessel including:
   a vessel body having an opening portion that communicates with the housing space;
   a lid that closes the opening portion; and
   a nozzle that passes through the lid and extends to the housing space, and supplies a liquid culture medium and a gas together,
   wherein the nozzle has a vent opening portion that is formed so as to open in a side wall of the nozzle and serves as a movement path of the gas from inside of the nozzle into the housing space,
   wherein the vessel body has a ceiling portion that covers above the housing space, and
   wherein the vent opening portion is formed so as to include an area above the ceiling portion.

2. The culture vessel according to claim 1,
   wherein the vent opening portion is configured with a side wall opening portion formed continuously or discontinuously from a tip opening portion provided in a tip portion of the nozzle.

3. A culture vessel having a housing space inside and used to culture cells within the housing space, the culture vessel including:
   a vessel body having an opening portion that communicates with the housing space;
   a lid that closes the opening portion; and
   a nozzle that passes through the lid and extends to the housing space, and supplies a liquid culture medium and a gas together,
   wherein the nozzle has a vent opening portion that is formed so as to open in a side wall of the nozzle and serves as a movement path of the gas from inside of the nozzle into the housing space,
   wherein the nozzle, on an inner face of the side wall, has a rib portion that protrudes toward an axial center of the nozzle, and
   wherein the rib portion is formed across a boundary portion between a formation area where the vent opening portion is formed in the axial direction of the nozzle and a non-formation area where the vent opening portion is not formed.

4. The culture vessel according to claim 1,
   wherein the lid includes an inner lid formed integrally with the nozzle, and an outer lid that is provided separately from the inner lid and fixes the inner lid by pressing the inner lid against the vessel body.

5. The culture vessel according to claim 1,
wherein the vessel body has a ceiling portion that covers above the housing space and a peripheral wall portion that covers the periphery of the housing space.

6. The culture vessel according to claim 5,
wherein the vessel body has a tubular portion that protrudes from the ceiling portion or the peripheral wall portion, and that protruding end forms the opening portion.

7. The culture vessel according to claim 1,
wherein the nozzle is provided so as to pass through a central position of the lid.

8. The culture vessel according to claim 1,
wherein the vessel body has a bottom portion that covers below the housing space, and
wherein a cell culture area is provided in a central side of the bottom portion, and a culture medium guide portion inclined downward toward the cell culture area is formed at a peripheral edge of the cell culture area.

9. The culture vessel according to claim 8,
wherein the vessel body has a ceiling portion that covers above the housing space, and a tubular portion that protrudes from the ceiling portion, that protruding end forming the opening portion,
wherein the tubular portion being formed so as to protrude upward from the ceiling portion, and
wherein the tubular portion and the nozzle being disposed at a position overlapping the culture medium guide portion when viewed in the vertical direction.

10. A cell culture device comprising a liquid feeding portion that supplies a liquid culture medium to a housing space of a culture vessel that cultures cells within the housing space, a liquid discharging portion that discharges the liquid culture medium from the housing space, a gas feeding portion that supplies gas to the housing space, a gas discharging portion that discharges the gas from the housing space, and a heat retaining portion that retains heat of the culture vessel,
the cell culture device being configured such that the liquid culture medium supplied from the liquid feeding portion and the gas supplied from the gas feeding portion are merged and supplied together,
wherein the culture vessel includes a vessel body having an opening portion that communicates with the housing space, a lid that closes the opening portion, and a nozzle for supply that passes through the lid and extends to the housing space,
wherein the nozzle has a vent opening portion that is formed so as to open in a side wall of the nozzle and serves as a movement path of the gas from inside of the nozzle into the housing space,
wherein the vessel body has a ceiling portion that covers above the housing space, and
wherein the vent opening portion is formed so as to include an area above the ceiling portion.

11. The cell culture device according to claim 10,
wherein the vent opening portion is configured with a side wall opening portion formed continuously or discontinuously from a tip opening portion provided in a tip portion of the nozzle.

12. A cell culture device comprising a liquid feeding portion that supplies a liquid culture medium to a housing space of a culture vessel that cultures cells within the housing space, a liquid discharging portion that discharges the liquid culture medium from the housing space a, gas feeding portion that supplies gas to the housing space, a gas discharging portion that discharges the gas from the housing space, and a heat retaining portion that retains heat of the culture vessel,
the cell culture device being configured such that the liquid culture medium supplied from the liquid feeding portion and the gas supplied from the gas feeding portion are merged and supplied together,
wherein the culture vessel includes a vessel body having an opening portion that communicates with the housing space, a lid that closes the opening portion, and a nozzle for supply that passes through the lid and extends to the housing space,
wherein the nozzle has a vent opening portion that is formed so as to open in a side wall of the nozzle and serves as a movement path if the has from inside of the nozzle into the housing space,
wherein the nozzle, on an inner face of the side wall, has a rib portion that protrudes toward an axial center of the nozzle, and
wherein the rib portion is formed across a boundary portion between a formation area where the vent opening portion is formed in the axial direction of the nozzle and a non-formation area where the vent opening portion is not formed.

13. The cell culture device according to claim 10,
wherein the lid includes an inner lid formed integrally with the nozzle, and an outer lid that is provided separately from the inner lid and fixes the inner lid by pressing the inner lid against the vessel body.

14. The cell culture device according to claim 10,
wherein the vessel body has a ceiling portion that covers above the housing space and a peripheral wall portion that covers the periphery of the housing space.

15. The cell culture device according to claim 14,
wherein the vessel body has a tubular portion that protrudes from the ceiling portion or the peripheral wall portion, and that protruding end forms the opening portion.

16. The cell culture device according to claim 10,
wherein the nozzle is provided so as to pass through a central position of the lid.

17. The cell culture device according to claim 11,
wherein the vessel body has a bottom portion that covers below the housing space, and
wherein a cell culture area is provided in a central side of the bottom portion, and a culture medium guide portion inclined downward toward the cell culture area is formed at a peripheral edge of the cell culture area.

18. The cell culture device according to claim 17,
wherein the vessel body has a ceiling portion that covers above the housing space, and a tubular portion that protrudes from the ceiling portion, that protruding end forming the opening portion,
wherein the tubular portion being formed so as to protrude upward from the ceiling portion, and
wherein the tubular portion and the nozzle being disposed at a position overlapping the culture medium guide portion when viewed in the vertical direction.

* * * * *

UNITED STATES PATENT AND TRADEMARK OFFICE
CERTIFICATE OF CORRECTION

PATENT NO. : 11,795,427 B2
APPLICATION NO. : 16/982802
DATED : October 24, 2023
INVENTOR(S) : Ryohei Tsukada et al.

It is certified that error appears in the above-identified patent and that said Letters Patent is hereby corrected as shown below:

On the Title Page

Item (73), Assignee, Line 2, after "(JP)" insert -- ; Hitachi, Ltd., Tokyo (JP) --

Item (57), Column 2, Abstract, Line 6, delete "the" and insert -- the lid --

Item (57), Column 2, Abstract, Line 9, delete "side" and insert -- side wall --

In the Claims

Column 16, Line 2, Claim 12, delete: "space a," and insert -- space, a --

Column 16, Line 19, Claim 12, delete "if the has" and insert -- of the gas --

Column 16, Line 47, Claim 17, delete "claim 11," and insert -- claim 10, --

Signed and Sealed this
Second Day of January, 2024

*Katherine Kelly Vidal*

Katherine Kelly Vidal
*Director of the United States Patent and Trademark Office*